United States Patent [19]

Watmough et al.

[11] Patent Number: 4,646,756

[45] Date of Patent: Mar. 3, 1987

[54] ULTRA SOUND HYPERTHERMIA DEVICE

[75] Inventors: David J. Watmough, Banchary; John R. Mallard, Aberdeen, both of United Kingdom; Kullevro Hynynen, Pyhanta, Finland

[73] Assignees: The University of Aberdeen; Carlton Medical Products Ltd., both of United Kingdom

[21] Appl. No.: 544,820

[22] Filed: Oct. 24, 1983

[30] Foreign Application Priority Data

Oct. 26, 1982 [GB] United Kingdom ............... 8230536
Aug. 10, 1983 [GB] United Kingdom ............... 8321547

[51] Int. Cl.$^4$ ................................................ A61N 1/00
[52] U.S. Cl. .................................. 128/804; 128/24 A
[58] Field of Search ............... 128/24 A, 76.5, 422, 128/660, 661, 804

[56] References Cited

U.S. PATENT DOCUMENTS

| | | | |
|---|---|---|---|
| 3,237,623 | 3/1966 | Gordon | 128/24 A |
| 3,561,430 | 2/1971 | Filler | 128/661 |
| 4,228,809 | 10/1980 | Paghzne | 128/804 |
| 4,282,880 | 8/1981 | Gardineer et al. | 128/660 |
| 4,311,154 | 1/1982 | Sterzer et al. | 128/804 |
| 4,315,514 | 2/1982 | Drewes et al. | 128/24 A |
| 4,397,314 | 8/1983 | Vaguine | 128/804 |

FOREIGN PATENT DOCUMENTS

| | | | |
|---|---|---|---|
| 8001462 | 7/1980 | Int'l Pat. Institute | 128/422 |
| 820814 | 12/1956 | United Kingdom . | |

OTHER PUBLICATIONS

British Journal of Cancer 1982, vol. 45, Supplement V. pp. 68–70.
Radiation & Environment Biophysics, vol. 19, pp. 215–226, 1981.

*Primary Examiner*—Edward M. Coven
*Assistant Examiner*—Max E. Hindenburg
*Attorney, Agent, or Firm*—Ostrolenk, Faber, Gerb & Soffen

[57] ABSTRACT

An ultrasound unit for the clinical application of hyperthermia to tumor cells in soft tissue. The ultrasound hyperthermic unit includes in one aspect an array of sonic transducers (1) radially disposed about an axis and angled to direct sonic energy (12) towards said axis at a point remote from said array, each transducer being adapted for angular movement relative to the other transducers thereby to allow adjustment of the shape of the acoustic focus. The array is computer controlled both with regard to acoustic focus and with regard to the energy imparted by each member of the array, said control being mediated by temperatures sensing means (40) adjacent a tumor. This ultrasound unit may be associated with a heat treatment tank (51, 31) including a flexible membrane (32, 52) which may overlie a tumor, thereby to locally raise the temperature and reduce the amount of ultrasonic power required to achieve a desired temperature. Suitable adjustment of the focused energy raises the temperature of the tumor cells above viability whereas the same temperature applied to healthy cells still allows viability by virtue of their relatively greater heat dissipation ability.

7 Claims, 7 Drawing Figures

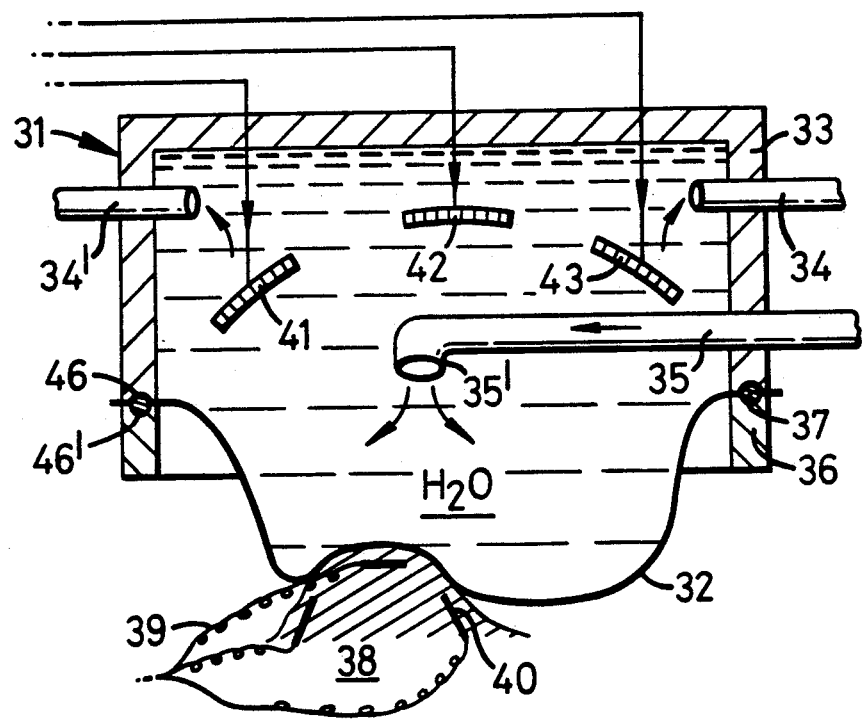

ULTRA SOUND HYPERTHERMIA DEVICE

BACKGROUND OF THE INVENTION

1. Field of the Invention

The present invention relates to an ultrasound unit for the clinical application of hyperthermia to tumor cells in soft tissues.

2. Background Art

Ultrasound units for the destruction of cells are known per se, from GB-A No. 820814. These are primarily designed for use in surgery and operate to totally destroy all tissue at the point of acoustic focus.

It is known that ultrasound is useful in raising tissue temperature to values typically between 42° and 48° C., but to higher temperatures if desirable. In the lower part of this range healthy tissue is able to dissipate the heat by virtue, inter alia, of arterial dilation and hence may remain comparatively undamaged. Necrosed and neoplastic tissues, however, have a limited, non-existent or non-elastic blood supply, and hence overheat. This causes selective death of these tissues. Even at the peripheral edges of a tumor where blood supply tends to be disproportionally high, the lack of arterial dilation assists in the death of these tissues.

It has been known, for example, from the British Journal of Cancer 1982 Vol. 45 Supplement V. P68-70 to provide an array of radially disposed sonic transducers which provide intersecting beams of sonic energy spaced some 50 mm into a model target, i.e. at the point of acoustic focus. When this array was used on a liver tissue sample with normal blood flow, it was found that maximum temperature was not obtained at the acoustic focus because, it is believed, blood supply to the intervening healthy tissue reduced the temperature increase.

However, as may be seen from Radiation & Environment Biophysics, Vol. 19, P215-266 1981, tumor tissue has varying densities and blood flow characteristics. Non-uniform temperature distribution in practice occurs, therefore, and this leads to the well perfused regions of tumor tissue escaping effective treatment.

SUMMARY OF THE INVENTION

The present invention seeks to alleviate this problem by providing a sensitive device which can regulate the adjacent areas of the acoustic focus to provide the desired temperature values in neoplastic regions of non-uniform density and blood supply.

According to the present invention, therefore, there is provided an ultrasound hyperthermia unit including ultrasound transducer means angled to direct sonic energy towards an acoustic focus, temperature sensing means for association with the point of acoustic focus and adapted to provide an output signal indicative of temperature values, the arrangement being such that said output signal is utilized to control the power output and the position of the acoustic focus to achieve localized heating of tumor tissues above viability.

Thus, the shape and power of the acoustic focus can be adjusted to take account of the density and shape of neoplastic tissues.

In a further embodiment, the power output of each transducer is individually controlled so that the energy imparted to tumor tissues of varying densities may be more accurately adjusted to prevent damage to adjacent healthy cells.

The transducer means may be an array which is conveniently controlled by an on-line microprocessor. To this end, each of the sonic transducers may be motor driven through an arc and/or an angle, while signal strength is controlled by a signal amplifier having a single output for each transducer. The whole system may also be motorized to move the focus throughout the tumor volume.

The temperature sensing means may, for example, be thermocouples to be provided at suitable positions adjacent, and preferably within, the tumor tissue and surrounding healthy tissues; said sensing means being adapted to provide a regular output indicative of the temperature values of the tissues in which they are positioned. Temperature values may also be monitored by indirect, non-invasive radiation sensing devices known per se.

Regular output signals from the sensors may be fed to the microprocessor which then controls the angle of the sonic transducers and their sonic output accordingly. The sonic output of each transducer may be in the range of 0.25 to 5 MHz, although ranges of between 0.5 and 1.5 MHz are generally found to be more desirable for tumors at a depth.

In a most preferred embodiment, the power to the ultrasonic transducers is momentarily switched off while the temperature sensing means output their values so that said values are not modified by the acoustic input per se.

The arrays of the above type are quite satisfactory for tumors in positions where there are no sensitive underlying tissues or organs, and where patient tolerance is not a problem. However, many tumors are in positions where there are good reasons for limiting the acoustic input and/or temperature levels, both because of patient tolerance and because ultrasound at higher inputs can cause hemolysis and other problems.

It has also been found, as a result of extensive testing, that patients may be acclimatized to the temperatures expected during ultrasonic treatment by gradually and locally raising the tissues on the skin surface adjacent a tumor to a desired temperature level, e.g. 41°–43° C. This may be effected according to a further independent feature of the invention by providing a heat treatment apparatus comprising a treatment tank provided with means for controlling the temperature of a heat exchange fluid circulatable therethrough, and a flexible heat conductive membrane forming part of said tank, whereby with the membrane overlying a portion to be treated, controlled heat from the heat exchange fluid can be applied to said portion even if said portion is irregularly shaped.

The heat treatment apparatus may itself be adapted for the treatment of tumors. In this case, it is desirable to limit the temperature range to a maximum value of about 48° C. as this is the maximum useful temperature. Of course if the heat treatment apparatus is used for purposes other than tumor treatment, i.e. in an industrial application, much higher temperatures can be accommodated.

For medical uses, however, the membrane may be made of any suitable heat resistant flexible and/or resilient plastics membrane which is of a thickness and strength sufficient to overlie irregularly shaped objects and mold to the contours thereof, while still maintaining its structural integrity.

Preferably the tank is formed of a plastics material which is conveniently "Perplex" (Registered Trade Mark); and is provided with an outlet or outlets preferably adjacent the uppermost portion of the tank in use. The tank is also provided with an inlet which preferably terminates about the vertical axis of symmetry of the tank in a downwardly directed nozzle. This ensures that the hot heat exchange fluid, which is preferably water, circulates about the membrane before rising to the outlet. By adjusting the speed of the pump and temperature of the water, a constant temperature value at the membrane interface can be achieved.

The heat exchange fluid is most preferably driven by a pump, for example a peristaltic pump. A heat exchange fluid reservoir may be provided remote from said heat treatment tank; a water heater being provided therein, the arrangement being such that water circulating from said heat treatment tank enters the reservoir, is re-heated, and returned to the heat treatment tank via a suitable pump means.

In a most preferred embodiment of the invention, the heat treatment tank and its associated apparatus are controlled by a microprocessor. To this end, temperature sensing devices such as thermistors are provided, for example, in the heat treatment tank, in the reservoir and in the fluid outlet. All these may be preset to a desired value and the microprocessor is therefore able to control both the heater in the reservoir and the pump to control the membrane temperature. The microprocessor may also be provided with a warning device, which may be a loudspeaker, for example. Further, the membrane may be provided with a liquid crystal strip which provides visual indication of excessive temperature.

The Applicants have also found that for many medical applications, improved sensitivity and lower power inputs can be achieved by combining the array as hereinbefore set forth with the heat treatment apparatus as described since this combination increases patient tolerance while, because the temperature of the skin is held near the desired temperature, decreasing the amount of acoustic power required.

Since it is often most desirable to limit the acoustic input because of collateral damage, this combination is particularly advantageous.

According therefore to a further feature of the invention, an ultrasound hyperthermia unit including an ultrasound transducer means angled to direct sonic energy towards an acoustic focus, a heat treatment tank provided with means for controlling the temperature of a heat exchange fluid circulatable therethrough, and a flexible heat conductive membrane forming part of said tank is provided, whereby with the membrane overlying a body portion to be treated, controlled heat from said heat exchange fluid can be applied to said portion while said ultrasound transducer means is directing sonic energy towards said acoustic focus within said portion.

In a most preferred form of the invention, the contact surface is a flexible heat conductive membrane forming part of a tank to constitute said bath as hereinbefore set forth. The particular features and methods of control specified above are generally applicable to the combined system just described but of course higher levels of control are possible within the system because it can be controlled by a single microprocessor and the various inputs correlated.

It will also be appreciated that because of the high efficiency of the blood system as a refrigerant where the tumor tissue is at or adjacent the skin surface, the outer surface of the tumor never really reaches its intended temperature because of conduction and radiation unless the above combined system is utilized.

According to a final feature of the present invention, there is provided a method for the controlled treatment of necrosed tissue by ultrasound hyperthermia which comprises focusing acoustic energy to a focal point within the necrosed tissue, positioning a plurality of temperature sensors adjacent or within the necrosed tissue, said sensors providing a temperature dependent output signal, processing said signal and adjusting the power output and acoustic focus of the acoustic energy in response to said signals to achieve localized heating of the necrosed tissue above its viability levels, while not exceeding the viability levels of adjacent healthy tissue.

BRIEF DESCRIPTION OF THE DRAWINGS

The invention will now be described, by way of illustration only, with reference to the accompanying drawings, wherein:

FIG. 7 shows a vertical cross-section through a combined heat treatment and ultrasonic transducer array.

DESCRIPTION OF PREFERRED EMBODIMENTS

Figure 1:
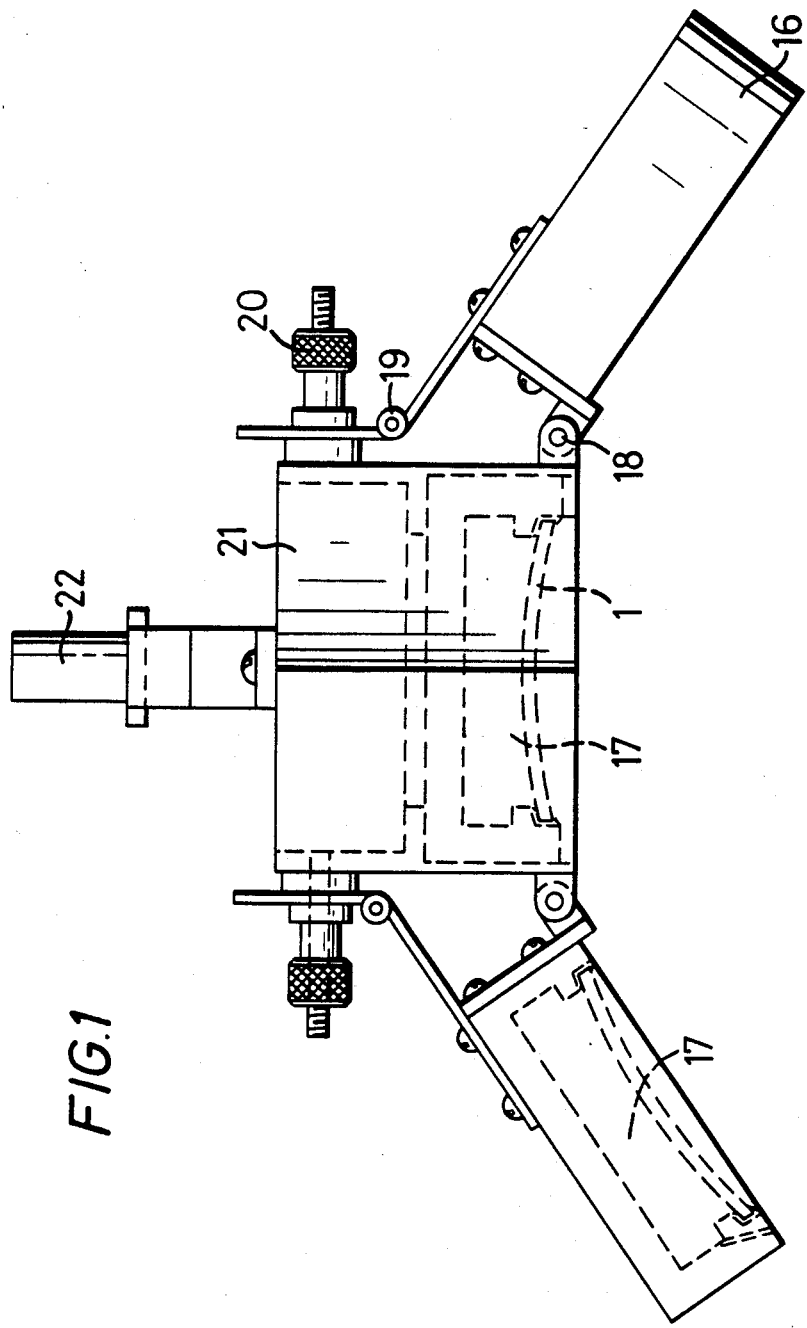
FIG. 1 shows a vertical view in part cross-section of the transducer element array of the invention, but with the stepping motor omitted for clarity.
Figure 2:
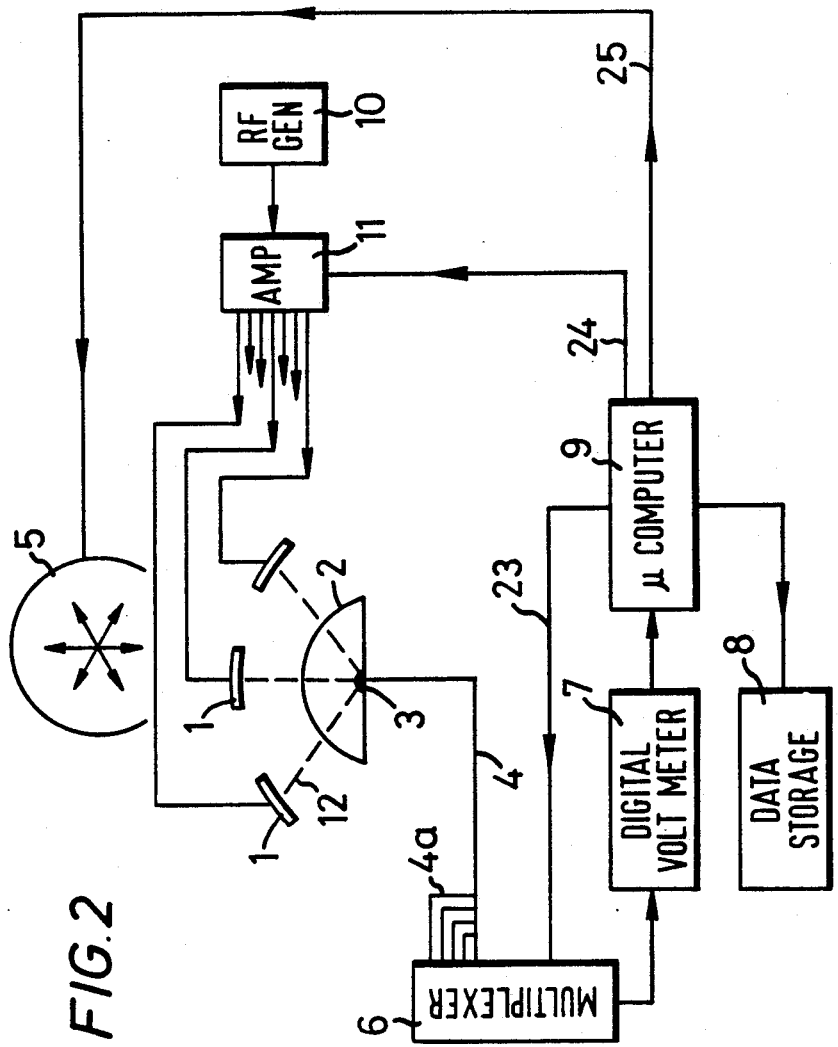
FIG. 2 shows a diagrammatic view of the hyperthermia unit including the array of FIG. 1.

With reference to FIGS. 1 and 2 of the drawings, an array of seven parabolic or spherical sonic transducers 1 is set in a hexagonal body 21, substantially as shown in FIG. 1.

Six of the seven sonic transducers are disposed radially about the hexagonal body at equally spaced intervals and pivoted thereto at pivot point 18. A single axially disposed transducer is provided centrally and shares a common axis with the body 21. Each of the peripheral transducers is disposed in a transducer support 16 which has a generally rectangular vertical section accompanied by a generally circular transverse cross-section.

On the face of the support 16 remote from the transducer is located a hinge bracket 19 which is affixed at its lower edge to the support 16 while being hinged to a slotted upper portion retained against the body 21 by a locating screw and nut 20, whereby the slotted portion can slide relative to the body 21, thereby altering the relative angle of the support 16 about the pivot 18, and hence altering the beam angle of the sonic transducer.

A stepping motor shown generally at 5 in FIG. 2 is associated with each hinge bracket 19 to alter the relative angle of each transducer portion.

The stepping motor 5 is also associated with pinion 22 whereby the whole transducer array can be relatively positioned prior to fine "tuning" by relative movement of individual transducer supports 16.

The hexagonal body 21 and each transducer support 16 is provided on its under side with a recess 17 to provide an air backed parabolic sonic transducer 1 having a silvered lower and upper surface as is known in the art.

The whole array is made of a material which is inert to any fluid of immersion during use and in this case is fashioned of brass and hardwood. It is later envisaged many of the parts will be made of plastics moldings.

With particular reference to FIG. 2 each sonic transducer 1 is shown connected to an amplifier 11 which amplifies the sonic signal from an RF generator 10 thereby to form the beam 12 directed to a target shown generally at 3 disposed within a skin surface 2. Thermocouples 4 are positioned adjacent the target 3 thereby to provide a plurality of signal lines 4A through a multiplexer 6. Signals from the multiplexer are converted in a digital volt meter 7 and supplied to a microcomputer 9 which in addition to supplying data to data storage 8 supplies instructing signals to control the various functions of the array. Thus, one set of commands 23 acts to switch the multiplexer in response to a time signal. The line 24 acts on each of the signal outputs of the amplifier 11 in response to information input from the thermocouples, thereby to control the power of signals reaching each transducer 1. Line 25 acts upon the stepping motor 5 which acts to reposition the transducer array in accord with changing temperature profile recorded by the thermocouple.

In order to avoid spuriously high readings due to shear effects at the thermocouple junctions, the line 23 allows the multiplexer to receive thermocouple signals only when the ultrasonic power from amplifier 11 is temporarily suspended. Thus, thermocouple values are recorded at regular spaced intervals, while ultrasonic transmission is suspended.

Figure 3:
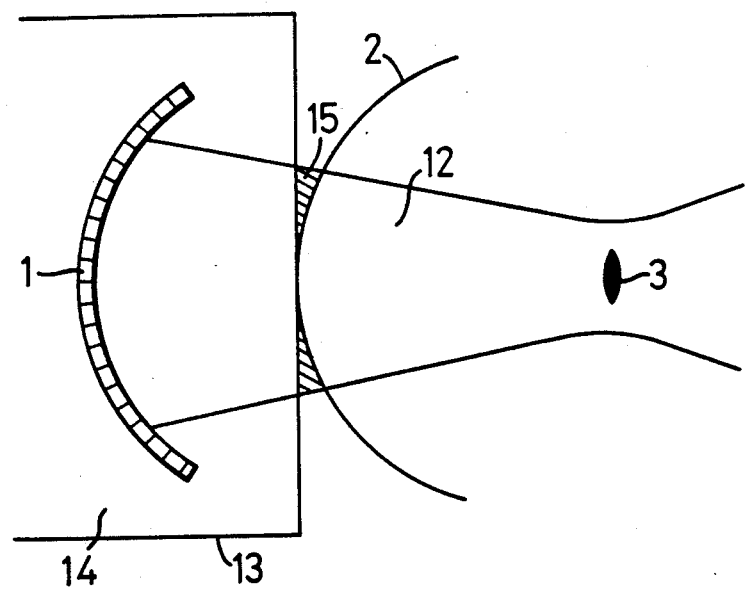
FIG. 3 shows a diagrammatic view of the unit of FIG. 2 in use.
Figure 4:
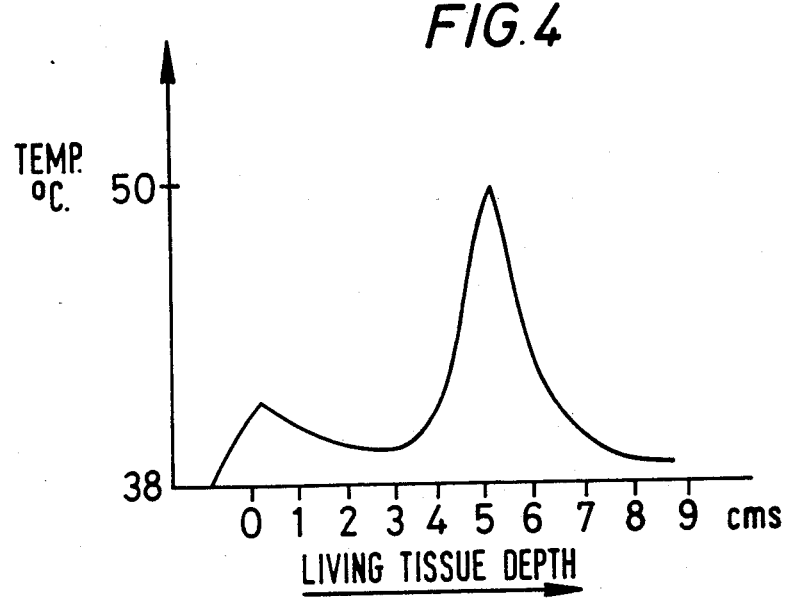
FIG. 4 shows a graph of tissue temperature with an acoustic focus set at 5.5 cms below skin surface.

With particular reference to FIG. 3 a single transducer or a multi-element array is disposed in de-gased water 14 contained in a thin polythene film shown diagrammatically at 13. Liquid crystals 15 are disposed on the skin surface 2 and are arranged to give warning of any abnormal heating of the skin which could cause burns. The sonic beam 12 generated from the transducer 1 is beamed toward the target 3. All six other sonic transducers are also beamed toward the target 3 and the temperature rise occasioned thereby is cumulative. This is best shown in FIG. 4 where the target depth is 5.5 cms and wherein all seven transducers are arranged to have their acoustic focus at 5.5 cms accordingly. It will be seen that a temperature approaching 50° C. occurs only at the point of acoustic focus.

Figure 5:
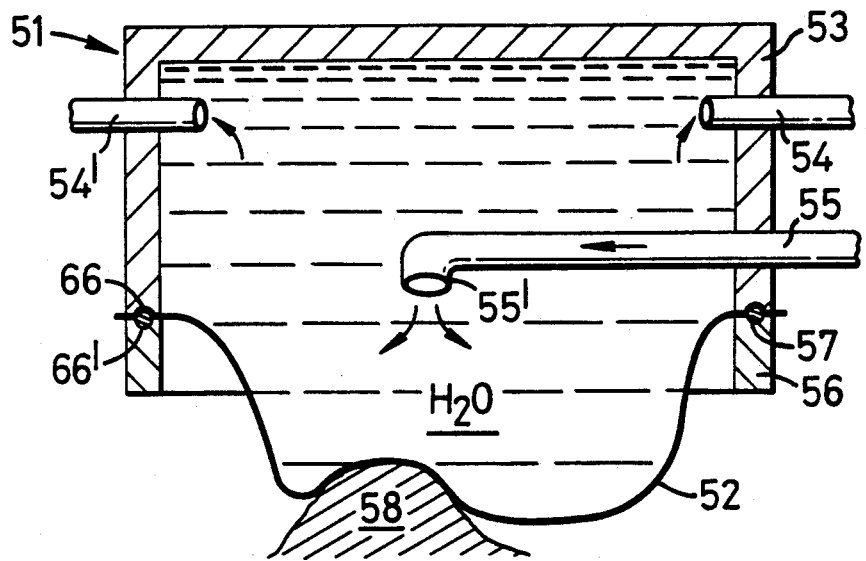
FIG. 5 is a vertical cross-section through a heat treatment device in accordance with a second aspect of the present invention.
Figure 6:
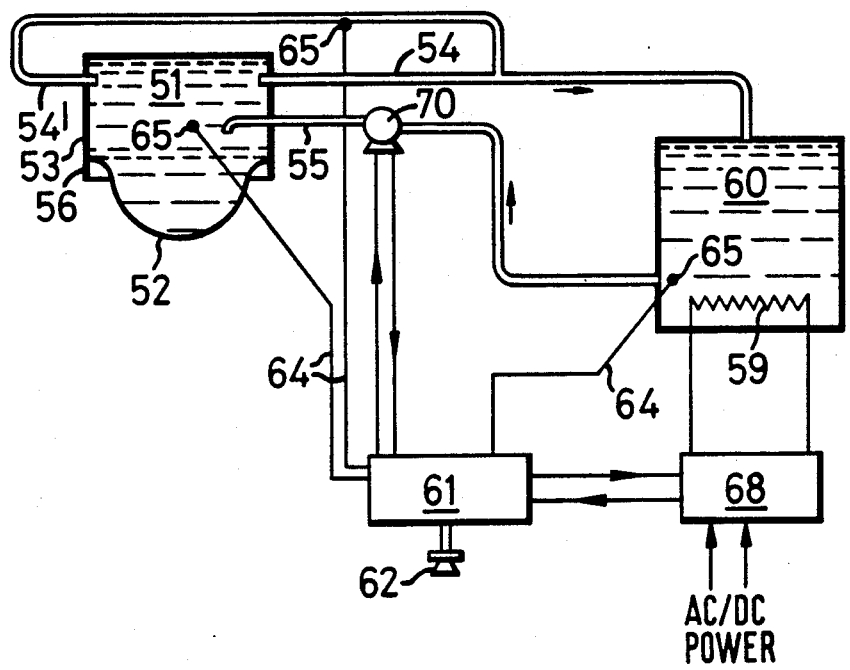
FIG. 6 shows a diagram of the heat treatment device and its associated control means.

With reference particularly to FIGS. 5 and 6, a substantially rectangular heat treatment tank 51 is provided with a substantially U-shaped member 53 terminating along its lower edges in a recess 66. The recess 66 is adapted to accommodate a sealing O-ring 57 which in turn is adapted to lie within the recess 66' in a member 56 which is clampable to the member 53 in use. The members 53 and 56 and the O-ring 57 clamp a flexible membrane 52 in a water-tight fashion. The membrane 52 and the tank 51 are all formed of a transparent material or materials.

The tank 51 is provided with a heat exchange fluid inlet 55, the end of which is downwardly directed about the axis of symmetry of the tank. Outlets 54 and 54' are provided remote from the membrane 52 parallel with the inlet 55 whereby fluid flow is first directed downwardly towards the membrane 52 and only subsequently upwardly to the outlets 54 and 54'. A downwardly directed nozzle piece 55' of the inlet 55 may be slightly offset so as to produce swirl in a downwardly directed fashion if desired.

It will be appreciated that with the temperature controlled to say 43° C., heat exchange fluid flows over the membrane 52 which in turn is disposed about a surface tumor 58 in or on the patient. The continual presence over a long period of temperatures of this value, which can be tolerated by a patient, can gradually destroy the tumor without significantly affecting adjacent tissue.

With reference now to FIG. 6, a microprocessor 61 is provided to control the heat treatment tank 51. The microprocessor is provided with control means for a switch 68 which switch also supplies power to a heater 59 disposed in a heat exchange fluid (water) reservoir 60. Thermistors 65 are also provided at key points throughout the system and supply signals to the microprocessor via lines 64. The microprocessor also controls peristaltic pump 70 so as to control the volume of heated liquid reaching the membrane 52. It will be readily appreciated that if a new temperature is set on the microprocessor, for example 43° C. when a previous value was 46° C., pump 70 may be switched off along with the heater 59 until the value falls the necessary 3°. The system can then be adjusted by the microprocessor 61 to supply water at the correct temperature.

Since it is important that the temperature of the localized heating at the membrane does not exceed 48° C., a thermistor positioned in the tank 51 is provided with override means which activates a loud speaker 62 via the microprocessor 61 if this temperature is exceeded. As a further fail-safe, a liquid crystal stripe is provided on the membrane. The patient may be instructed that if this stripe changes color, the temperature of the tank is in excess of the desired treatment temperature and hence he may call for assistance.

The device may be used to acclimatize the patient to the temperatures experienced during ultrasonic therapy deeper in the soft tissues. It has been found that treatment of tumors with ultrasonics can be barely tolerated if high power inputs, and hence high temperatures, are utilized. This tolerance, however, can be increased if the patient is acclimatized to high temperatures before treatment and accordingly where a tumor is seated well below the surface of the skin it may be desirable to utilize the apparatus of the present invention to acclimatize the patient to high temperatures so that primary treatment with ultrasonics can proceed without patient distress.

With reference particularly to FIG. 7, the substantially rectangular heat treatment tank 31 is provided with a substantially U-shaped member 33 terminating along its lower edges in a recess 46. The recess 46 is adapted to accommodate a sealing O-ring 37 which in turn is adapted to lie within the recess 46' in the member 36 which is clampable to the member 33 in use. The members 36 and 33 and the O-ring 37 clamp a flexible membrane 32 in a water-tight fashion. The membrane 32 and the tank 31 are all formed of a transparent material or materials.

The tank 31 is provided with a heat exchange fluid inlet 35 the end of which is downwardly directed about the axis of symmetry of the tank. Outlets 34 and 34' are provided remote from the membrane 32 parallel with the inlet 35 whereby fluid flow is directed first downwardly towards the membrane 32 and only subsequently upwardly to the outlets 34 and 34'. The downwardly directed nozzle piece 35' of the inlet 35 may be slightly offset so as to produce swirl in a downwardly directed fashion if desired.

It will be appreciated that with the temperature controlled to say 43° C., heat exchange fluid flows over the membrane 32 which in turn is disposed about the surface tumor 38 in the patient. An array of ultrasonic transducers 41, 42, 43 is also positioned within the tank 33. These are shown as a concave array which is focusable but may in some circumstances be a single concave transducer or one or more convex transducers where for example the tumor overlies a particularly sensitive body organ.

Similarly to the arrangements shown in FIGS. 2, 3 and 6, a microprocessor is provided to control the heat treatment tank and the ultrasonic array. The microprocessor is provided with control means for a switch which switch also supplies power to a heater disposed in a heat exchange fluid (water) reservoir. Thermistors are provided at key points throughout the system and supply signals to the microprocessor via respective lines. The microprocessor also controls a peristaltic pump so as to control the volume of heated liquid reaching the membrane. It will be readily appreciated that if a new temperature is set on a microprocessor, for example 43° C. when a previous value was 46° C., the pump may be switched off along with the heat until the desired value falls the necessary 3° C. Similarly, the ultrasonic transducers are controlled by the same microprocessor in a fashion set out in FIGS. 1 to 4, but with an array of temperature sensors 40, positioned in and about the tumor tissue 38, and connected to the microprocessor via leads 39.

Whereas the transducer array has been described as being set within the heat treatment tank, assemblies wherein the transducer array is exterior to the heat treatment tank can be useful in some applications.

By use of the combined system just described, a high patient tolerance can be achieved and hence treatments can be more prolonged. This is important since the surgical process of insertion of the thermocouples into the tumor is uncomfortable and should not be repeated any more frequently than necessary.

What is claimed is:

1. An ultrasound hyperthermia unit for treatment of tumors comprising:
   (a) ultrasound transducer means comprising an angled array of ultrasonic transducers, each transducer being individually movable, the ultrasound transducer means being angled for directing sonic energy toward an ultrasound acoustic focus, and the ultrasound acoustic focus being movable to substantially all locations within a tumor to be treated by moving the transducers individually;
   (b) drive means for moving the individually movable transducers;
   (c) temperature sensing means for sensing temperature within the tumor and for providing a signal indicative of temperature at a plurality of locations within the tumor; and
   (d) a control circuit for receiving the signal indicative of temperature and for controlling the ultrasound transducer means and drive means, the control circuit being operable in response to the signal indicative of temperature for:
      (1) controlling the power output of sonic energy by the ultrasound transducer means toward the ultrasound acoustic focus; and
      (2) controlling the drive means to treat such tumor by automatically moving the transducers individually, to move the ultrasound acoustic focus to substantially all locations throughout the tumor volume for localized heating of tumor tissues above viability by controlled application of sonic energy; and
   (e) the ultrasound acoustic focus and the sonic energy output being jointly controlled to raise the temperature of substantially all portions of the tumor to above the temperature of viability, each portion being heated substantially only long enough to kill such portion, tumor portions having nonuniform physical characteristics and blood supply being differentially treated to avoid substantial overheating.

2. A unit as in claim 1, wherein the sonic energy from said ultrasound transducer means heats such tumor tissues without being sufficient to cause substantial cavitation thereof.

3. An ultrasound hyperthermia unit for treatment of tumors comprising:
   (a) an ultrasound transducer comprising a concave array of elements, each element being individually movable, the elements of the ultrasound transducer being angled for directing sonic energy toward an ultrasound acoustic focus, and the ultrasound acoustic focus being movable to substantially all parts of a tumor to be treated by moving the elements individually;
   (b) drive means for moving the individually movable elements;
   (c) a temperature sensing array for sensing the temperature within the tumor and for providing a signal indicative of temperature at a plurality of locations within the tumor;
   (d) a heat treatment tank for containing a heat exchange fluid, the tank comprising a flexible heat conductive member for overlying the tumor to be treated for applying heat from the heat exchange fluid to raise the temperature of the skin adjacent the tumor;
   (e) means for changing the temperature of the heat exchange fluid; and
   (f) a control circuit for receiving the signal indicative of temperature and for controlling the ultrasound transducer, the drive means and the temperature changing means, the control circuit being operable in response to the signal indicative of temperature for:
      (i) controlling the drive means to position the ultrasound acoustic focus within the tumor and for
      (ii) controlling the heat applied to the skin adjacent the tumor by controlling the temperature changing means to change the temperature of the heat exchange fluid, while controlling the ultrasound transducer to direct sonic energy toward the ultrasound acoustic focus within the tumor;
   (g) the drive means being controlled to treat such tumor by automatically moving the ultrasonic acoustic focus to substantially all locations throughout the tumor volume for localized treatment of tumor tissues above the temperature of viability, the temperature of each such portion being raised to above viability substantially only long enough to kill such portion, tumor portions having non-uniform physical characteristics and blood supply being differentially treated to avoid substantial overheating, and the sonic energy coacting with the heat applied by the heat treatment tank to carry out such heating.

4. A unit as in claim 3, wherein the sonic energy from said ultrasound transducer means heats such tumor tissues without being sufficient to cause substantial cavitation thereof.

5. A method for the controlled treatment of tissue by ultrasound hyperthermia comprising:
positioning a plurality of temperature sensors to sense the temperature at a plurality of locations within the tissue, the sensors providing a temperature dependent output signal;
individually adjusting each of an array of transducer elements to focus ultrasound acoustic energy from the transducer elements on an ultrasound acoustic focus within the tissue;
processing the temperature dependent output signal to obtain temperature information; and
adjusting the power output of ultrasound acoustic energy by the transducer elements and individually adjusting each of the array of transducer elements in response to the temperature information to move the ultrasound acoustic focus to a plurality of locations within the tissue to achieve localized heating of the tissue at each such location to above its viability levels substantially only long enough to kill such tissue while not exceeding the viability levels of adjacent healthy tissue.

6. The method of claim 5 further comprising:
applying a flexible heating jacket to skin adjacent the tissue; and
passing heated fluid through the flexible heating jacket to bring the skin to a temperature of approximately 41°–43° C. during the application of the ultrasound acoustic energy to coact with such energy to carry out such heating.

7. A method as in claim 5, including heating such tissue without applying sufficient sonic energy to cause substantial cavitation thereof.

* * * * *